(12) United States Patent
Kirkpatrick et al.

(10) Patent No.: US 9,095,289 B2
(45) Date of Patent: Aug. 4, 2015

(54) DENTAL X-RAY AIMING DEVICE WITH MARGINAL RIDGE INDEXING

(76) Inventors: Steven Kent Kirkpatrick, Placerville, CA (US); Roger John Koughan, Fairplay, CA (US)

(*) Notice: Subject to any disclaimer, the term of this patent is extended or adjusted under 35 U.S.C. 154(b) by 403 days.

(21) Appl. No.: 13/573,292

(22) Filed: Sep. 7, 2012

(65) Prior Publication Data

US 2013/0071809 A1 Mar. 21, 2013

Related U.S. Application Data

(60) Provisional application No. 61/573,908, filed on Sep. 13, 2011.

(51) Int. Cl.
*A61B 6/14* (2006.01)
*A61B 6/00* (2006.01)

(52) U.S. Cl.
CPC . *A61B 6/145* (2013.01); *A61B 6/14* (2013.01); *A61B 6/4435* (2013.01); *A61B 6/44* (2013.01); *A61B 6/587* (2013.01)

(58) Field of Classification Search
CPC .... A61B 6/145; A61B 6/4429; A61B 6/4435; A61B 6/4441; G03B 42/04; G03B 42/042
USPC ........ 378/38–40, 168–170, 191, 205; 433/29, 433/215
See application file for complete search history.

(56) References Cited

U.S. PATENT DOCUMENTS

| 2,553,028 | A | * | 5/1951 | Wright | 378/170 |
| 3,473,026 | A | | 10/1969 | Updegrave | |
| 4,554,676 | A | * | 11/1985 | Maldonado et al. | 378/170 |
| 5,001,738 | A | * | 3/1991 | Brooks | 378/170 |
| 5,327,477 | A | * | 7/1994 | Levy | 378/168 |
| 5,652,779 | A | | 7/1997 | Levy | |
| 6,190,042 | B1 | * | 2/2001 | Dove et al. | 378/170 |
| 7,819,579 | B2 | * | 10/2010 | Schmulenson et al. | 378/170 |
| 7,871,199 | B2 | | 1/2011 | Szommer | |
| 7,959,354 | B2 | | 6/2011 | Steward, Jr. et al. | |
| 8,016,483 | B2 | | 9/2011 | Steward, Jr. | |
| 2009/0168953 | A1 | * | 7/2009 | Szommer | 378/38 |
| 2010/0027756 | A1 | | 2/2010 | Hof | |
| 2010/0177875 | A1 | * | 7/2010 | Steward et al. | 378/170 |

OTHER PUBLICATIONS

Flow Dental Catalogue 2012 Deer Park NY USA p. 7,9.

* cited by examiner

*Primary Examiner* — Robert Kim
*Assistant Examiner* — David E Smith

(57) ABSTRACT

The present invention is a device for aiming a dental x-ray beam to be centered parallel to the area of contact between two adjacent teeth so that the resultant bite wing radiographic image is one that shows at least those two teeth as distinct and not superimposed images. The device, comprising a marginal ridge angulation locator that indexes into the substantially v-shaped groove on the biting surfaces between two adjacent teeth, locates and indicates an aiming vector centered over and parallel to the area of contact between those two teeth for the purpose of aiming an x-ray beam then exposing the radiographic image desired.

23 Claims, 15 Drawing Sheets

DENTAL X-RAY AIMING DEVICE WITH MARGINAL RIDGE INDEXING

BACKGROUND

One of the major challenges during the taking of a bitewing radiograph is to open the contact between teeth. In other words to expose a radiograph that shows the teeth as distinct teeth and not have portions of teeth overlapped or superimposed on each other. This goal has been elusive for many people taking bitewing x-rays. This invention makes it easier for someone to take an ideal bitewing x-ray.

SUMMARY

The present invention is an aiming device to assist in aiming dental x-rays parallel to and centered over the area of contact between two adjacent human teeth for the purpose of exposing a radiographic image of at least those two teeth as substantially distinct individual teeth and not superimposed on each other in the image. The present invention comprises a marginal ridge angulation locator attached to the superior or inferior surface of a first platform that is configured to fit into and be stabilized in the substantially "V" cross section shaped groove on the biting or occlusal surface defined by the area of contact of the adjacent marginal ridges of two adjacent teeth in a human mouth, called the occlusal groove. When the upper and the lower teeth are closed together against the first platform it will be stabilized so that the marginal ridge angulation locator stays motionless in the occlusal groove. Once stabilized in the occlusal groove, the marginal ridge angulation locator has located and indicates a vector, the aiming vector, parallel to and centered over the area of contact between two adjacent teeth. Further, a second platform comprising a medial surface and a lateral surface, comprising at least one attachment location on the lateral surface and configured to be capable of holding a dental x-ray film or dental x-ray sensor against its medial surface is flexibly and removably attached substantially perpendicular to the first platform by a flexible pivot stud on the medial aspect of the first platform that allows the first platform a range of motion of as much as 10 to 15 degrees relative to the second platform in the occlusal plane. The second platform when attached to the first platform is configured to fit into a human mouth on the lingual side between tongue and teeth while the first platform is stabilized between the biting surfaces of the teeth. The first platform further comprises a marginal ridge angulation indicator capable of demonstrating a first vector that is parallel to the aiming vector that was located by the marginal ridge angulation locator. The first vector may be co-located or displaced from the aiming vector. Further, an x-ray beam may be aligned parallel to the first vector, parallel to and centered over the aiming vector and thus capable of exposing an image of at least two distinct individual adjacent teeth whose images are not superimposed or overlapped. In another preferred aspect the second platform comprises as many as 5 or more attachment locations that allow the first platform to be attached to the second platform in a configuration that facilitates the taking of horizontal bite wing, vertical bite wing, horizontal peri-apical or vertical peri-apical radiographs. In one embodiment the attachment locations on the second platform are configured as holes. In other embodiments the attachment locations are configured as holes that may be round, square, octagonal or other cross section shaped holes. In another aspect the pivot stud on the first platform comprises an insert end that may be inserted into one of the attachment locations, hole, of the second platform removed and rotated 0, 90, 180 or another chosen amount of angular rotation and reinserted into the same or another attachment hole on the lateral surface of the second platform. In another aspect the flexible pivot stud on the first platform in conjunction with the corresponding attachment hole on the lateral surface of the second platform allow a range of motion in the horizontal plane of as much as 10 to 15 or more degrees due to the relative shapes of the holes or the flexibility of the pivot stud or both. In another embodiment the attachment locations on the second platform comprise a positive shape such as a stud and the corresponding shape of the end of the pivot stud comprises a negative space such as a hole. In another aspect, the marginal ridge angulation locator comprises a triangular cross section, a somewhat triangular shaped cross section a round shaped cross section, a semi round shaped cross section or some other shape cross section configured to fit into the occlusal groove with its somewhat triangular shaped cross section. In another aspect an angulation indication extension may be attached either removably or permanently to the angulation indicator, which locates the first vector. The angulation indication extension may be bent, curved or straight and may locate a second vector anterior to the first vector and the aiming vector so that it is more easily viewed from outside the mouth. In another aspect the angulation indication extension further comprises a ring shaped device, a disc shaped device or a planar device that when attached either removably or permanently to the angulation indication extension has its center located directly over and its plane perpendicular to the aiming vector. In another aspect the ring shaped or disc shaped device is configured to be capable of being attached to the angulation indication extension configured as a rod collocated with the second vector. The ring or disc shaped device of this embodiment is configured to be able to stay centered over the aiming vector and perpendicular to it while sliding to and being fixed at different positions along the rod.

The present invention also provides a dental radiographic system comprising an x-ray generating device or x-ray machine, a dental x-ray film packet or dental x-ray sensor or both, a device for viewing the image such as an x-ray view box or a video viewing device further comprising a computer, software program to convert information generated by the sensor to be able to be viewed on the video screen or printed on a printer and the dental x-ray aiming device with sensor or film holder.

The present invention comprises a specific method for its use comprising attaching the dental x-ray sensor to the medial surface of the second platform, attaching the flexible pivot stud to the central attachment location on the lateral surface of the second platform, positioning the marginal ridge angulation locator in the occlusal groove and having the patient bite down seating the marginal ridge angulation locator into the occlusal groove, attaching the angulation indication extension to the angulation indicator, aiming the x-ray beam parallel to the angulation indicator and centered over the aiming vector, then triggering the x-ray machine causing the x-rays to emit form the x-ray machine parallel to the aiming vector and parallel to the contact area between the two adjacent teeth causing an image of two substantially distinct and not overlapped or superimposed teeth. In another embodiment the marginal ridge angulation locator, configured to be rotatably attached to the superior surface of the first platform, has an axis of rotation perpendicular to the first platform and substantially parallel to the long axis of the teeth that are holding the first platform. In another embodiment the marginal ridge angulation locator is flexibly attached to the lateral surface of the first platform and configured so that it rests slightly above the first platform and is able to flex enough to allow it to seat into the substantially triangular cross section shape of the occlusal groove between two adjacent teeth and locate the aiming vector. In another embodiment the attachment end of the flexible pivot stud is configured so that it snaps into an attachment hole and both are configured to allow the first platform a range of motion relative to the second platform of 10 to 15degrees or more in the horizontal plane and very little or not movement in the vertical plane. All embodiments comprise molded or machined parts that may comprise a hard plastic, a soft plastic a, a soft rubber like material, a stickey soft material, a composite material, a metallic material, a radiolucent material and or a radiopaque material. Some embodiments comprise combinations of different materials. Some of the materials may be suitable for multiple use after sterilization and other materials may be suitable for only single use. In another embodiment the marginal ridge angulation locator comprises a very thin knife-edge shape. Another embodiment comprises a first platform comprising a very soft plastic or rubbery material that may be sticky as well surrounding a harder substance forming the marginal ridge angulation locator. Another embodiment comprises a marginal ridge angulation locator that comprises either a continuous bar with somewhat triangular cross sectional shape or an interrupted bar with a somewhat triangular cross sectional shape. Another embodiment comprising at least one groove and possibly a plurality of parallel and or perpendicular non-intersecting grooves that are shaped to be capable of retaining an appropriately shaped end of the flexible pivot stud and allow the stud to slide along the groove and at least one point on each groove allow the pivot stud to be removed and rotated either 0, 90 or 180 degrees and then be re inserted into that or another groove.

BRIEF DESCRIPTION OF DRAWINGS

FIG. 29.

DETAILED DESCRIPTION

In the following description, the use of "a," "an,", or "the" can refer to the plural. All examples given are for clarification only, and are not intended to limit the scope of the invention.

Figure 1:
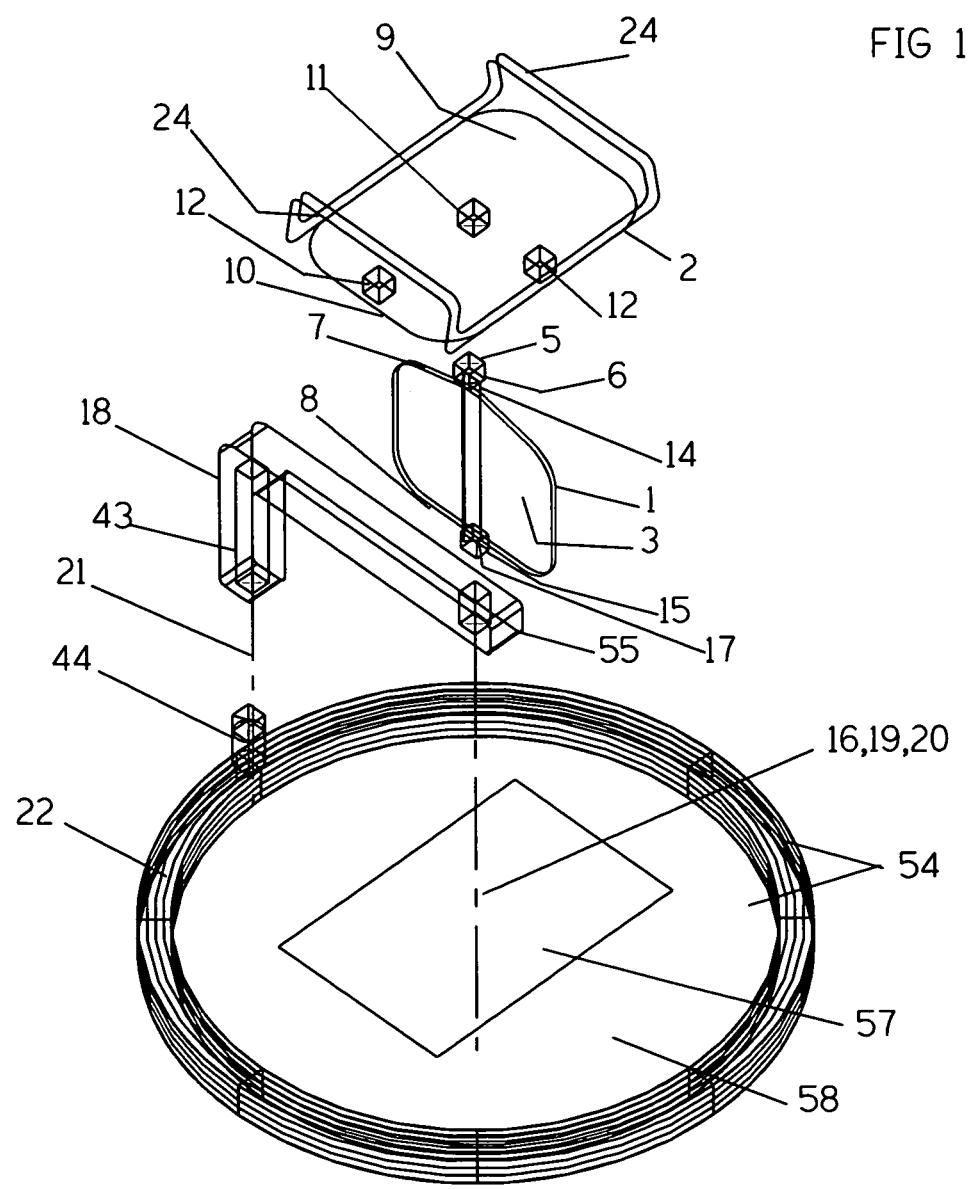
FIG. 1. is an exploded isometric view of one embodiment of the aiming device.

FIG. 1 Is an exploded isometric view of the aiming device showing a first platform (1) with a top surface (3), a bottom surface (4), a medial edge (7) and a lateral edge (8) further comprising a flexible pivot stud (6) attached to the medial edge (7) of the first platform (1). The medial end of the flexible pivot stud (6) comprises an attachment end (5). Also illustrated is a second platform (2) comprising a medial side (9) and a lateral side (10). The medial side (9) of the second platform (2) could comprise a retainer (24) or a plurality of retainers (24) each configured to securely hold a dental x-ray sensor or dental x-ray film packet. The lateral side (10) of the second platform (2) further comprises at least one attachment location (11). The one attachment location positioned at the center of the lateral side (10) of the second platform (2) further the lateral side (10) of the second platform (2) may in addition comprise a plurality of attachment locations (12) in various locations on the lateral side (10) of the second platform (2). The attachment end (5) of the flexible pivot stud (6) is configured to be able to be either removably attached or it may be configured to be permanently attached to the central attachment location (11) on the lateral side (10) of the second platform (2) in such a manner that the first platform (1) is substantially perpendicular to the second platform (2). The attachment end (5) of the flexible pivot stud (6) in one preferred embodiment is configured to be removably attached to the central attachment location (11). The attachment end (5) may be removed from the central attachment location (11) and attached to another of the attachment locations (12) on the lateral surface (10) of the second platform (2). Additionally, the first platform (1) comprising a marginal ridge angulation locator (13) configured to be capable of defining an aiming vector (19) further comprising a long axis (16) parallel to the aiming vector (19) that may be located and attached to the first platform (1) on the top surface (3) or the bottom surface (4) of the first platform (1). By way of example and not limitation, the marginal ridge angulation locator (13) in one preferred embodiment extends laterally from approximately the lateral end (14) of the flexible pivot stud (6) to approximately the lateral edge (8) of the first platform. Further, attached to the lateral edge (8) of the first platform (1) is an angulation indicator (15) with an attachment stud (17) capable of indicating the long axis (16) defined by the marginal ridge angulation locator (13) and additionally capable of defining a first vector (20) parallel to the aiming vector (19) that may or may not be collocated with the aiming vector (19). Further, by way of example and not limitation, in one preferred embodiment, there is an angulation indication extension (18) capable of being attached to the angulation indicator (15) that indicates a second vector (21) that is displaced some convenient distance from the first vector (20), that distance would be in the range of 1 to 2 inches. The second vector (21) is parallel to the aiming vector (19) and the first vector (20). Further, the angulation indication extension (18) may additionally comprise an aiming platform (54) that is fixed or removably attached to the angulation indication extension (18). The aiming platform comprising at least one aiming ring attachment location (44) that attaches to the extended rod end (43) of the angulation indication extension (18). The aiming platform (54) centered over and perpendicular to the aiming vector (19) may comprise a ring shape, rectangular shape or other external shape. The aiming platform may comprise a round or rectangular internal shape that may be shaped slightly larger than the outline of a particular size x-ray sensor or film. The space between the external shape and the internal shape of the aiming platform comprising at least one of a radio opaque metal, radio opaque composite and a radio opaque plastic with the purpose of blocking all but the necessary x-rays for exposing the desired image. The elements of this embodiment may comprise at least one of a plastic, silicone rubber, nitrile rubber, composite, paper and a metal.

Figure 2:
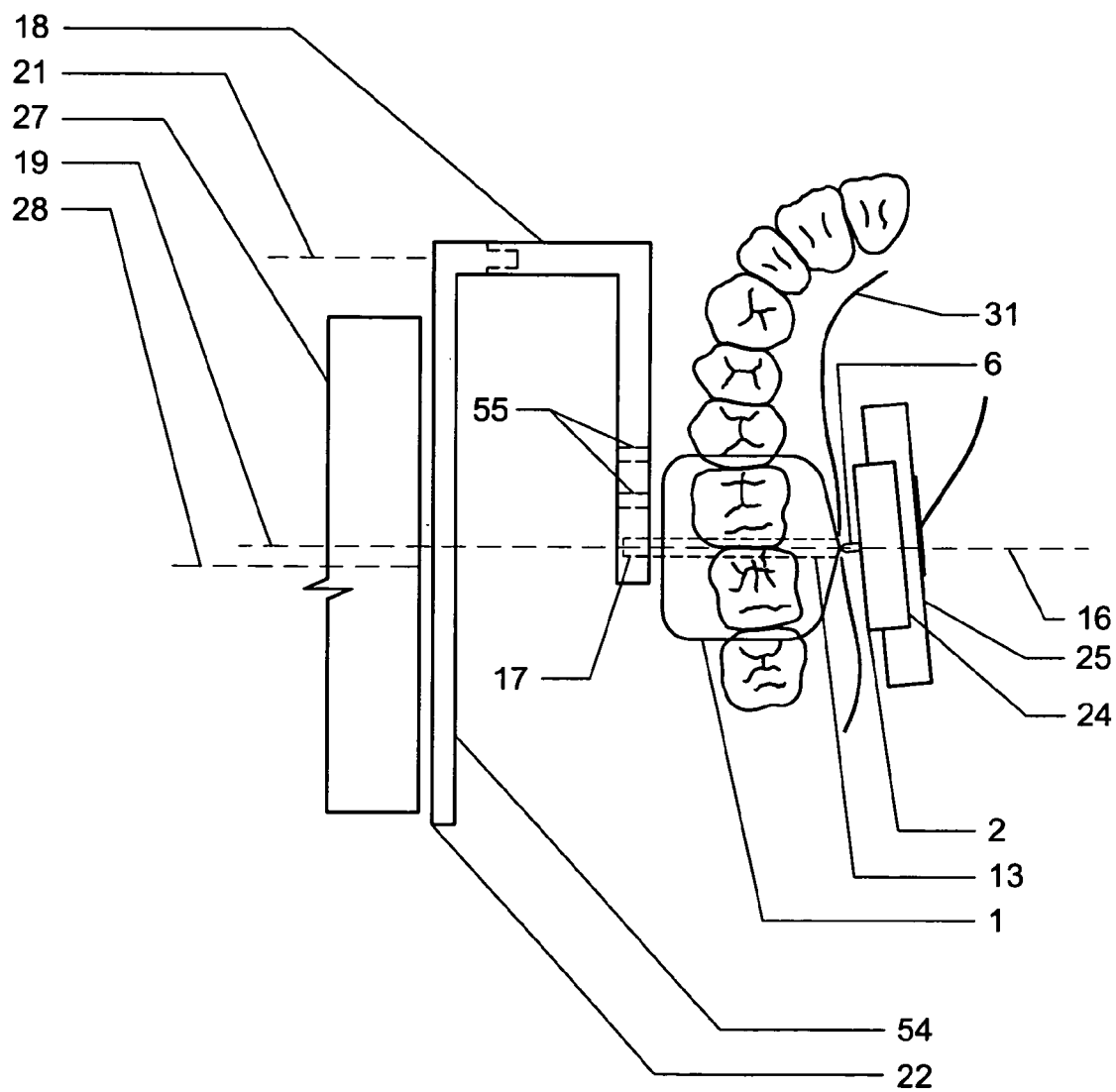
FIG. 2. is a top view of the aiming device in a human mouth.

Some elements may comprise materials that may be autoclavable and thus reusable and other elements may comprise materials that are not autoclavable and are thus single use elements. Some elements may comprise materials that may be steriliized by other methods known or not known today. Some elements may comprise materials that are radio opaque and other elements may comprise materials that are radiolucent. Further, elements of this invention may be injection molded and or machined FIG. 2 is a top view of the aiming device in a human mouth. In this figure the first platform (1) is lying superimposed over the first and second molars. By way of example and not limitation, the first platform is substantially planar and ranges in size from 0.75 inches square to as small as 0.5 inch by 0.375 inch and irregularly shaped FIG. 16. The marginal ridge angulation locator (13) is lying directly over the contact area (30) between the adjacent marginal ridges (29) of two adjacent molar teeth and the long axis (16) of the marginal ridge angulation locator (13) lies substantially parallel to the contact area (30) between the adjacent marginal ridges (29) of two adjacent teeth and identifies the aiming vector (19) that passes through the area where the two adjacent teeth contact and parallel to the area of contact, the contact area, (30) between the two adjacent teeth. The angulation indication extension (18) in this preferred embodiment comprising at least one attachment location (55) and possibly a plurality of attachment locations (55) each comprising a hole configured to be attached to the attachment stud (17) of the angulation indicator (15). The angulation indication extension (18) is configured so that when attached to the attachment stud (17) of the angulation indicator (15) to indicate the second vector (21) that is displaced in an anterior direction from and parallel to the aiming vector (19). The amount of anterior displacement caused by the shape of the angulation indication extension needs to be approximately ½ the diameter of an x-ray cone or between 1⅜ inches and 1⅝ inches to allow an aiming platform (54) that is the diameter of the x-ray tube (27) to be centered over the aiming vector. The contact area (30) in the example shown is not perpendicular to the line of the jaw (31). The line of the jaw (31) on one side of the jaw, is a line that is substantially parallel to a straight line running from anterior to posterior through the center of the alveolar ridge from the maxillary first pre molar through the maxillary second molar of that same side of the dental arch. It is known to those with experience in the art that the contact area (30) between maxillary molars is often not perpendicular to the line of the jaw (31). The flexible pivot stud (6) configured so that it may bend slightly to allow the marginal ridge angulation locator (13) to stay fixed parallel to the contact area (30) and parallel to the aiming vector (19) even though the angle between the long axis (16) of the marginal ridge angulation locator (13) and the second platform (2) may differ from 90 degrees. It is known in the art that the line of the jaw (31) is very often not perpendicular to the line defined by the contact area (30). By way of example and not limitation, in this preferred embodiment of the present invention, the flexible pivot stud (6) is flexible enough to allow as much as 10 to 15 degrees or more bending of the flexible pivot stud (6) in a plane that is substantially parallel to the plane of occlusion of the teeth. Flexibility of the flexible pivot stud (6) in this preferred embodiment is necessary to allow the second platform (2) and the attached dental x-ray sensor (25) to lie in the space between the tongue and the line of the jaw (31) in a human mouth at the same time that the long axis (16) of the marginal ridge angulation locator (13) is lying directly over and parallel to the contact area (30) between the adjacent marginal ridges (29) of two adjacent teeth. The flexible pivot stud (6) needs to be thin enough to allow flexibility and thick enough to prevent breakage, dimensions in the range of from 0.060 inch×0.060 inch to 0.120 inch×0.120 inch can be used. By way of example and not limitation, one preferred embodiment has a pivot stud with 0.100×0.100 inch. The area of attachment of the flexible pivot stud (6) to the relatively thinner first platform, with a thickness range of 0.010 inch or less to as much as 0.080 inch or more, (1) is a weak point that may require reinforcement not shown. By way of example and not limitation, one preferred embodiment comprising a first platform thickness of 0.020 inch allows more complete closure of the mandible in use. The aiming platform (54) in the shown preferred embodiment (FIG. 2) of the current invention is shown attached to the angulation indication extension (18) and configured to be able to be positioned perpendicular to and centered on the aiming vector (19) and the long axis (16) of the marginal ridge angulation locator (13). The dental x-ray cone (27) is shown positioned with the x-ray beam midline (28) centered on and parallel to the aiming vector (30). Configured in the manner shown in FIG. 2 and described herein when the x-ray machine is triggered the x-ray beam (23) will pass through the teeth and the contact area (30) between the teeth in such a manner that the image exposed on the film (26) or the sensor (25) will be that of substantially individual teeth that are not superimposed.

Figure 3:
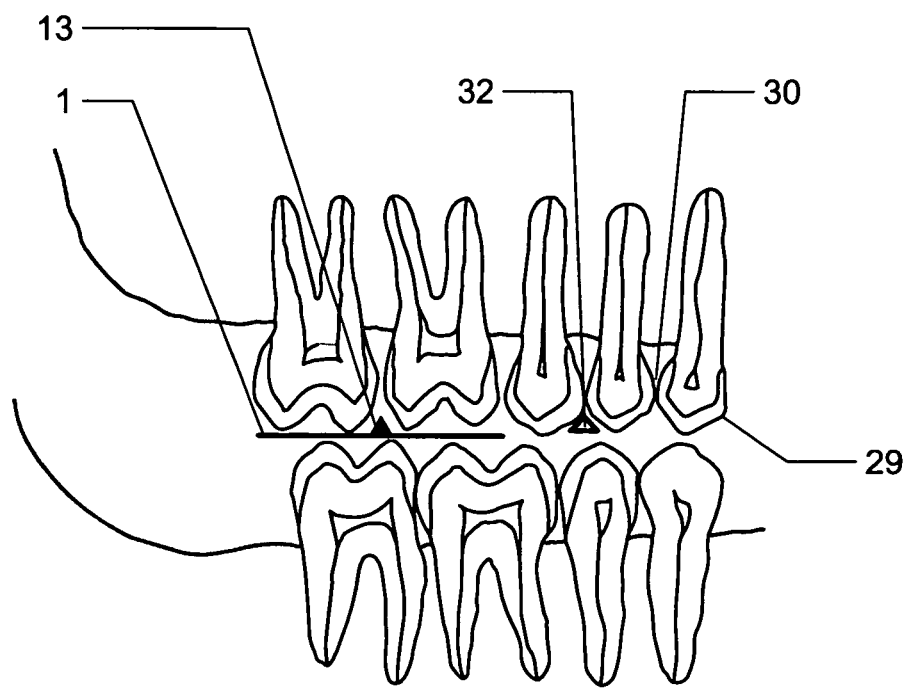
FIG. 3. is a lateral view of a dental arch with mandibular teeth closed into one embodiment of the first platform.

FIG. 3 is a lateral view of a dental arch with mandibular teeth closed onto one preferred embodiment of the first platform (1) comprising the marginal ridge angulation locator (13) comprising a substantially triangular shaped cross section nested into the substantially triangular cross sectional shape of an occlusal groove (32) on the occlusal surface of a dental arch. The occlusal groove is formed by the contact of the two adjacent marginal ridges (29) of 2 adjacent teeth. A substantially triangular shaped cross section could comprise a 20-60 degree angle at the apex and a height of from 0.030 inch to 0.120 inch. It is likely that even angles less than 20 degrees or larger angles than 60 degrees, perhaps as much as 90 degrees or more, would work well also. By way of example and not limitation, one preferred embodiment comprising a triangular cross sectional shaped ridge comprising a 30 degree angle at the apex and a height of 0.090 inch from the superior surface of the first platform to the apex has worked well. It is well known in the art that the occlusal groove (32) is substantially parallel to the contact area (30) between two adjacent teeth and thus would also be parallel to the aiming vector (19) required to successfully "open the contacts", a term used in the art to describe the primary goal of a bite wing x-ray, an image on a bite wing x-ray that shows the contact area (30) between two adjacent teeth and images of those teeth as substantially individual and not overlapping each other in the image. The first platform (1) comprising a flexible material with a thickness of from 0.010 inch or less to as much as 0.080 inch or more depending on flexibility, durometer rating, and strength. A thinner first platform (1) will allow the maxillary teeth and the mandibular teeth to rest closer together when they are holding the first platform (1) allowing the image to include more alveolar bone and less space between maxillary and mandibular teeth. For clarity, a dashed line outlines the position occupied by a dental x-ray sensor (25) or a dental x-ray film packet (26).

Figure 4:
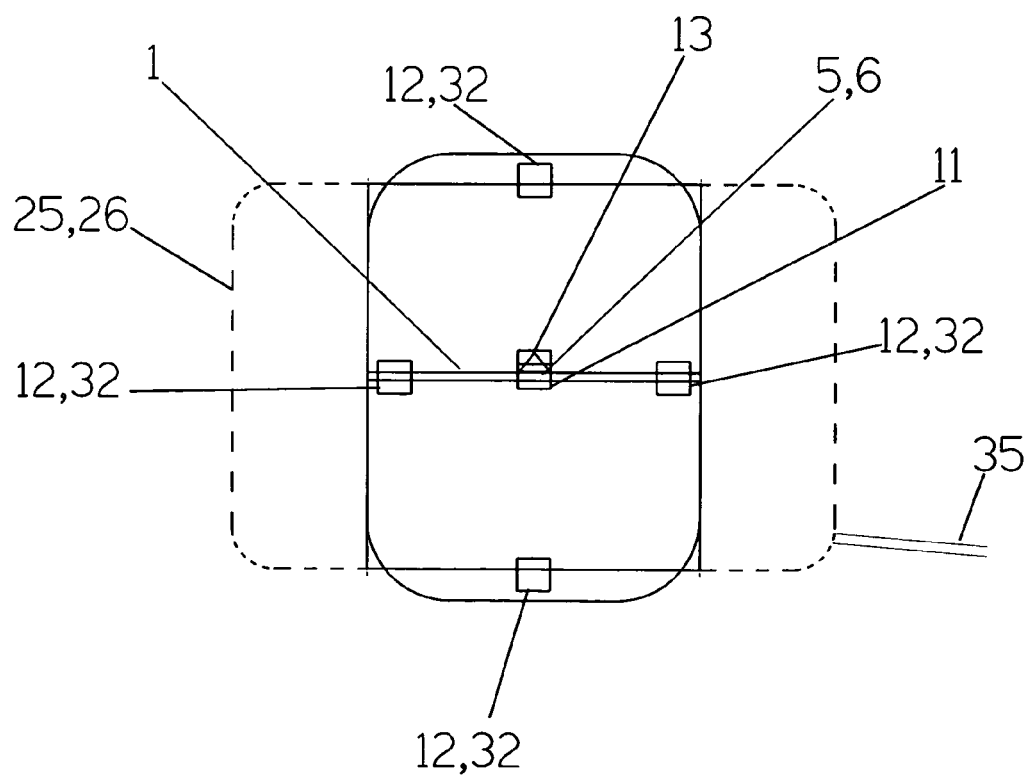
FIG. 4. is a lateral view of the second platform.

FIG. 4 shows a lateral view of the second platform (2) comprising the central attachment location (11) and the plurality attachment locations (12) each configured as a hole (32) in the second platform (2). Each of the holes in the second platform (2) may comprise at least one of a round shape cross section, a square shaped cross section, an octagonal shaped cross section or another cross sectional shape that may be deemed useful for the purposes of this invention. The holes are located to ease and expand the usefulness of the present embodiment of this invention. The dashed line in this drawing shows the position of a dental x-ray sensor (25) or film packet (26) centrally located on the second platform (2). Further, an end view of the first platform (1) with an end view of the marginal ridge angulation locator (13) is shown attached at the central attachment location (11) and a sensor cable (35) is shown coming from the end of the dental x-ray sensor (25). Configured in this manner, the aiming device is ideally suited for taking a horizontal bitewing on the right side of the mouth. If the attachment end (5) of the flexible pivot stud (6) of the first platform (1) is removed from the central attachment location (11) hole location and rotated 180 degrees around the long axis of the marginal ridge angulation locator (16) (seen better in FIGS. 1 and 2) and the reinserted in the same hole, the aiming device is ideally suited for taking a bite wing x-ray of the left side of the mouth. If the attachment end (5) of the flexible pivot stud (6) on the first platform (1) is removed rotated as above but only 90 degrees and reinserted in the hole at the central attachment location (11), the aiming device is ideally configured to take a vertical bitewing x-ray. In a similar manner, if the attachment end (5) of the flexible pivot stud (6) of the first platform (1) is removed from the central attachment location (11) and reinserted into one of the holes located at one of the plurality of attachment locations (12) the aiming device is ideally configured to take a periapical x-ray in either the horizontal orientation or the vertical orientation depending on which of the plurality of attachment locations (12) is chosen.

Figure 5:
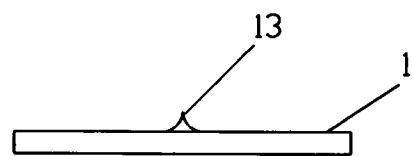
FIG. 5. is a lateral view of the first platform with somewhat triangular shaped cross section marginal ridge angulation locator.

FIG. 5 shows a lateral view of the first platform (1) with a somewhat triangular cross section shaped marginal ridge angulation locator (13) the angulation indicator (15) has been omitted from the drawing for clarity.

Figure 6:
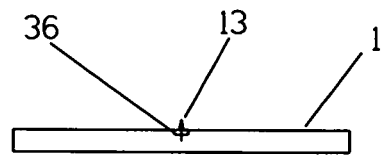
FIG. 6. is a lateral view of the first platform comprising a knife edge shaped marginal ridge angulation locator.

FIG. 6 shows a lateral view of the first platform (1) that comprises a knife-edge shaped cross section marginal ridge angulation locator (13). The included angle of the marginal ridge angulation locator (13) in this embodiment may be as small as 3 or 4 degrees and the height might be as little as 0.010 to 0.030 inches. This preferred embodiment comprising a formed insert (36) comprising a very hard composite material or a metallic material that extends into the rest of the first platform (1) for retention and stability. The hard edge of this preferred embodiment comprising a formed insert with a thickness of from 0.010 inch or less to as much as 0.040 inch or more could be used. This embodiment would be useful for locating the occlusal groove (32) when there is a severely worn dentition causing the occlusal groove (32) to be very shallow and narrow. For clarity the angulation indicator (15) has been omitted from the drawing.

Figure 7:
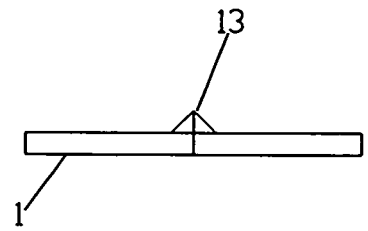
FIG. 7. is a lateral view of the first platform comprising a triangular shaped cross section marginal ridge angulation locator.

FIG. 7 shows the first platform (1) comprising a triangular shaped cross section marginal ridge angulation locator (13). The angulation indicator (15) has been omitted from the drawing for clarity.

Figure 8:
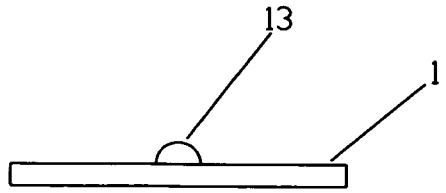
FIG. 8. is a lateral view of the first platform comprising a round shaped cross section marginal ridge angulation locator.

FIG. 8 shows the first platform (1) comprising semi round cross section marginal ridge angulation locator (13). The angulation indicator (15) has been omitted from this drawing for clarity.

Figure 9:
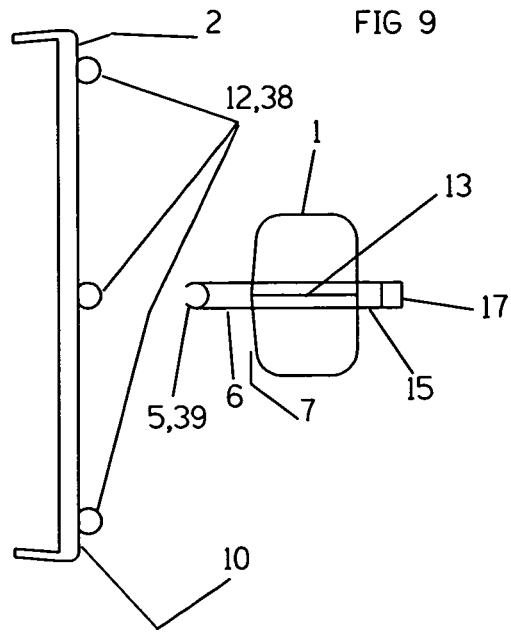
FIG. 9. is an exploded top view of the first and second platforms

FIG. 9 is an exploded top view of the first platform (1) and the second platform (2) configured to retain a dental x-ray film packet or dental x-ray sensor, connected together to take a vertical bitewing x-ray. In this referred embodiment the plurality of attachment locations (12) on the lateral side (10) of the second platform (2) are each configured as a positive shape, for example, a second platform attachment stud (38). The second platform attachment stud (38) or plurality of second platform attachment studs (38) may comprise at least one of, a square, round, hexagonal, octagonal and another shaped cross section as would benefit the usefulness of the current invention. The first platform (1) comprising the flexible pivot stud (6) attached to the medial edge (7) of the first platform further comprising the attachment end of the flexible pivot stud (5) that comprises a flexible pivot stud attachment hole (39) with a cross sectional shape comprising at least one of a round, square, hexagonal, octagonal and any other shape that would correspond, mate with and be removably attached in a secure fashion to the second platform attachment stud (38) and or the plurality of second platform attachment studs (38) of the second platform.

Figure 10:
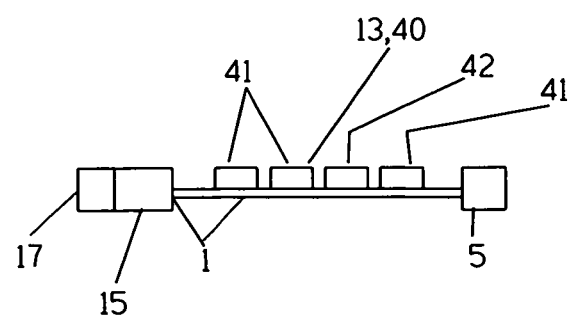
FIG. 10. is a side view of one embodiment of the first platform.

FIG. 10 is a side view of the first platform (1) comprising the marginal ridge angulation locator (13) further comprising an interrupted bar (40) with a roughly triangular cross sectional shape. The interrupted bar (40) shown in this preferred embodiment comprises a series of shorter bars (41) each with a roughly triangular cross section that are configured end to end with a space (42) between each shorter bar (41). Configured in this manner, the interrupted bar (40), depending on the radio opacity of the material comprising the shorter bars (41), length of each shorter bar (41) and the length of each space (42) will comprise a total radio opacity that is less than that of the marginal ridge angulation locator (13) shown in FIGS. 2, 5, 7 and 8. Decreasing the radio opacity of the marginal ridge angulation locator (13) in this manner may be advantageous in some circumstances. Further, the ability to compress or to bite into the bar may be adjusted by varying the ratio of the length of each shorter bar (41) to the length of each space (42). It is desirable to have the patient be able to close completely into the first platform (1) so that the maxillary teeth and the mandibular teeth come as close together as possible in order to use all available area on the sensor (25) not shown or x-ray film (26) not shown to image important anatomic structure rather than imaging a space between the biting surface between the occlusal surfaces of teeth that can provide no useful information.

Figure 11:
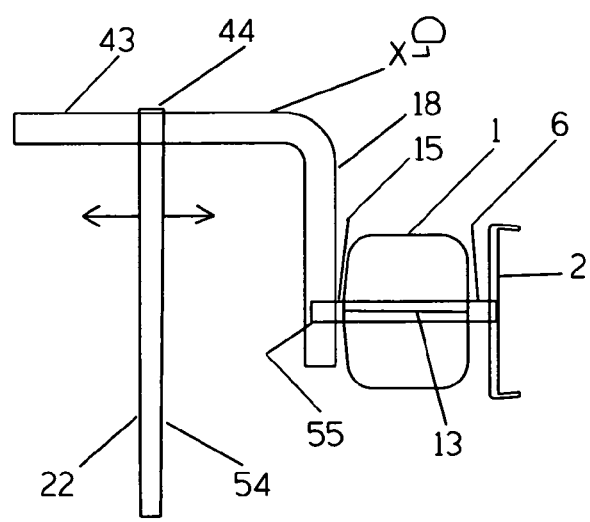
FIG. 11. is a top view of one embodiment of the aiming device.

FIG. 11 is a top view of the angulation indication extension (18) further comprising an extended rod end that is parallel to the aiming vector and coincident with the second vector. Also shown is the aiming platform (54) further comprising an aiming ring (22) and at least one aiming ring attachment location (44) and possibly a plurality of aiming ring attachment locations (44) configured to be movably (in a sliding manner), non-rotatably and removably (capable of being removed from) attached to the extended rod end (43) of the angulation indication extension (18). The extended rod end (43) and the aiming ring attachment location (44) comprise cross sectional shapes configured to allow the aiming ring attachment location (44) and aiming ring (22) to be slidable along the extended rod end (43) of the angulation indication extension (18) so that in use, the distance from the attachment point (55) on the angulation indication extension (18) to the aiming ring (22) is variable by as much as 2 or 3 inches and possibly more if needed and maintain the center of the aiming ring to remain over the aiming vector. Shown also are angulation indicator (15) of the first platform (1) attached to the angulation indication extension (18) and the second platform (2) attached to the attachment end (5) of flexible pivot stud (6) of the first platform. Shown also is the marginal ridge angulation locator (13) of the first platform.

Figure 12:
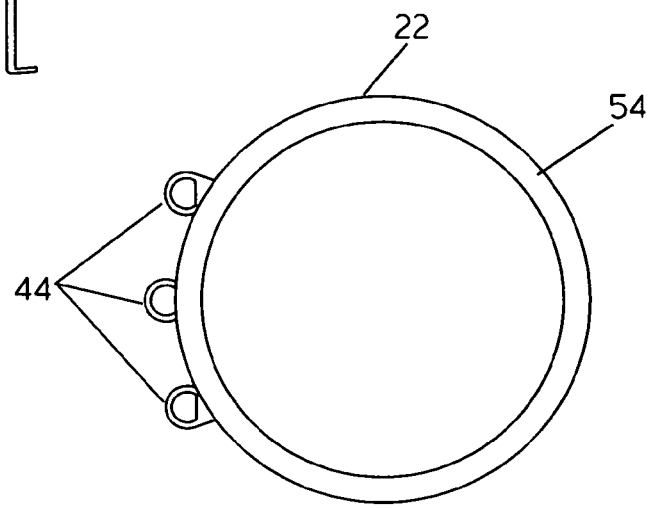
FIG. 12. is an end view of the aiming ring

FIG. 12 Further the shapes of the extended rod end (43) shown FIG. 11 and the corresponding internal shape of the aiming ring attachment location (44) are configured to permit the aiming ring (22) and the aiming ring attachment location (44) to be rotationally indexed relative to the extended rod end (43) shown FIG. 11 and thus also rotationally indexed to the aiming vector located by the marginal ridge angulation locator (13) on the first platform (1) when attached. The attachment collar (44) and or plurality of aiming ring attachment locations (44) comprise physical orientation or orientations to the aiming ring (22) and an internal cross sectional shape or shapes that allow the aiming ring (22) to be at least one of, positioned perpendicular to and centered over the aiming vector (19) for taking a horizontal bite wing x-ray, a vertical bite wing x-ray, a horizontal peri-apical x ray and a vertical peri-apical x-ray using the procedure described in the description for FIG. 4.

Figure 13:
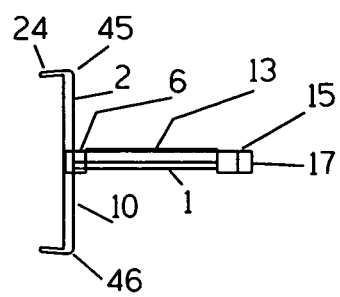
FIG. 13. is a lateral side view of one embodiment of the aiming device.

FIG. 13 is a lateral side view of this preferred embodiment of the current invention. The first platform (1) is permanently and non flexibly attached perpendicular to the the second platform (2) comprising a top edge of the second platform (45) and a bottom edge of the second platform (46) and is configured to retain a dental film packet or a dental x-ray sensor, permanently and non-flexibly attached substantially perpendicular to the first platform in an orientation that places it approximately half the distance between and parallel to the top edge of the second platform (45) and the bottom edge of the second platform (46). Further, the second platform (2) comprising the marginal ridge angulation locator (13) permanently and flexibly attached to the lateral side (10) of the second platform perpendicular to the second platform (2) and parallel to the plane of the first platform (1) by the flexible pivot stud (6). The marginal ridge angulation locator (13) in this embodiment is attached just above the top surface (3) of the first platform and comprises an angulation indicator (15) with an attachment stud on the angulation indicator (17) configured to be able to attach the angulation indicator extension (18). When placed into a human mouth the flexibility afforded marginal ridge angulation indicator (13) allows it to seat into the occlusal groove and indicate the aiming vector while the first platform is gripped between the teeth to stabilize the aiming device.

Figure 14:
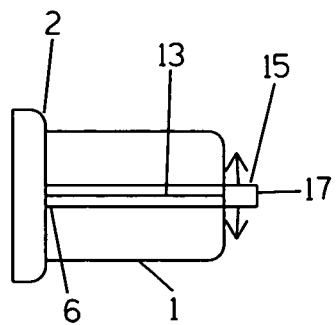
FIG. 14. is a top view of the same embodiment shown in FIG. 13.

FIG. 14 is a top view of the first platform (1) attached to the second platform (2) with the marginal ridge angulation locator (13) attached to the second platform (2) by the flexible pivot stud (6). The marginal ridge angulation locator (13) further comprising the angulation indicator (15) and the attachment stud on the angulation indicator (17) is able to move through and angle of 10 to 15 degrees from perpendicular relative to the lateral side of the second platform (10).

Figure 15:
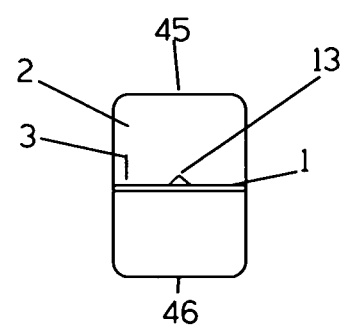
FIG. 15. is an end view of the same embodiment shown in FIG. 13 and FIG. 14.

FIG. 15 is a side view of the second platform (2) with the top edge of the second platform (45) and the bottom edge of the second platform (46) and showing the first platform (1) lying perpendicular to the second platform (2) with the marginal ridge angulation indicator (13) lying just superficial to the top surface of the first platform (3)

Figure 16:
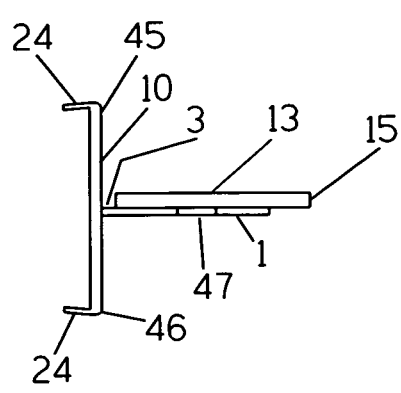
FIG. 16. is a side view of one embodiment of the aiming device.

FIG. 16 is an end view of the first platform (1) permanently and non-flexibly attached perpendicular to the plane of the second platform (2) and positioned so that the first platform (1) is attached to the second platform (2) approximately equidistant from the top edge of the second platform (45) and the bottom edge of the second platform (46) and parallel to both top and bottom edges. The first platform (1) of this embodiment of the current invention comprising a marginal ridge angulation locator (13) that is rotatably attached to the top surface of first platform (3) and very close to the first platform (1) by a rotatable stud (47) configured to be rotatable through a range of approximately plus or minus 10 to 15 degrees or more from perpendicular relative to the lateral side (10) of the second platform (2) while at the same time keeping the long axis (16) of the marginal ridge angulation locator (13) approximately parallel to the first platform (1). The marginal ridge angulation locator (13) further comprising an angulation indicator (15) at its lateral end configured to be capable of holding the angulation indication extension (18). The second platform (2) of this embodiment of the present invention further comprises at least one retainer (24) and possibly a plurality of retainers (24) configured to be able to hold a dental x-ray film packet (26) and or a dental x-ray sensor (25).

Figure 17:
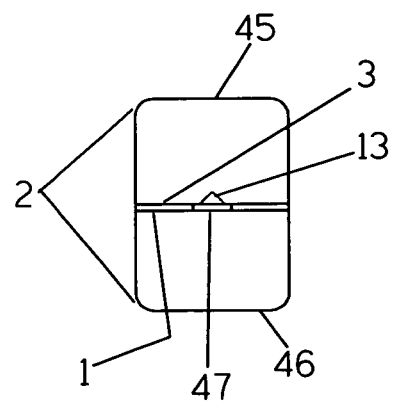
FIG. 17. is a lateral view of the same embodiment shown in FIG. 16.

FIG. 17 is a side view of the same embodiment shown in FIG. 16 showing the second platform (2) with the top edge of the second platform (45) and the bottom edge of the second platform (46) and the first platform (1) attached perpendicular to the second platform (2). The marginal ridge angulation locator (13) is shown attached to the first platform (1) by the rotatable stud (47) that passes through and is rotatable in the first platform (1).

Figure 18:
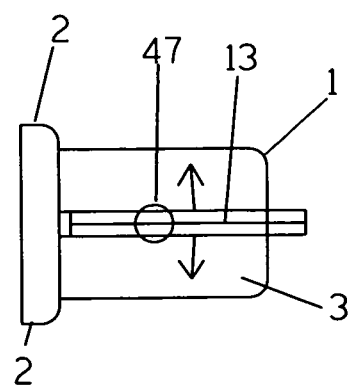
FIG. 18. is a top view of the same embodiment shown is FIG. 16 and FIG. 17.

FIG. 18 is a top view of the same embodiment shown in FIGS. 16 and 17 showing the first platform (1) with the marginal ridge angulation locator (13) over the top surface of the first platform (3) and the rotatable stud (47) that holds the marginal ridge angulation locator (13) and allows it to rotate in the plane parallel to the first platform (1) and perpendicular to the second platform (2). Configured in this manner the marginal ridge angulation locator (13) may be seated into the occlusal groove and indicate an aiming vector while the first platform (1) is stabilized between the upper and lower teeth and the second platform (2) capable holding an x-ray sensor or film allows the image to be exposed.

Figure 19:
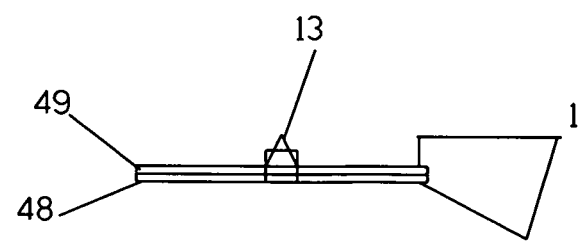
FIG. 19 is a lateral view of one embodiment of the aiming device.

FIG. 19 is a top view of one embodiment of the first platform (1) comprising a relatively flexible plastic base layer (48) further comprising the marginal ridge angulation locator (13) comprising the same or a similar material and the base layer (48) covered by a second layer (49) comprising a softer more compressible plastic material that further may have a sticky or tacky surface and that leaves at least some of the marginal ridge angulation locator (13) exposed to aid in positioning the first platform (1) in the mouth with the marginal ridge angulation locator (13) seated in the occlusal groove (32). The soft layer (49) covering the more stiff but yet flexible base layer (48) allowing the operator to better feel the marginal ridge angulation locator (13), made of a harder material, seating into the occlusal groove (32). After the marginal ridge angulation locator (13) is seated into the occlusal groove (32) the second layer (49), comprising a softer material, enabling the maxillary and mandibular teeth to close more fully into the base layer (48), thus fully stabilizing the marginal ridge angulation locator (13) in the occlusal groove (32) and reducing the distance between the maxillary and the mandibular teeth for the bite wing x-ray image.

Figure 20:
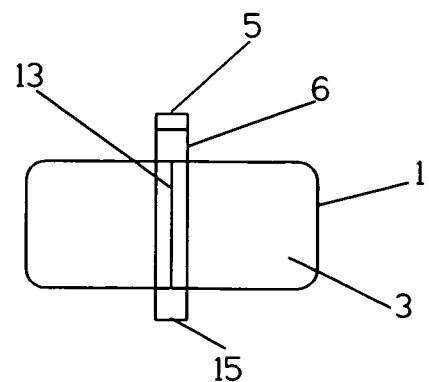
FIG. 20. is a top view of the same embodiment shown is FIG. 19.

FIG. 20 is a top view of the same embodiment shown in FIG. 19 with the first platform (1) further comprising the marginal ridge angulation locator (13) attached to the top surface of the first platform (3) and the flexible pivot stud (6) with the attachment end of the flexible pivot stud (5) and the angulation indicator (15).

Figure 21:
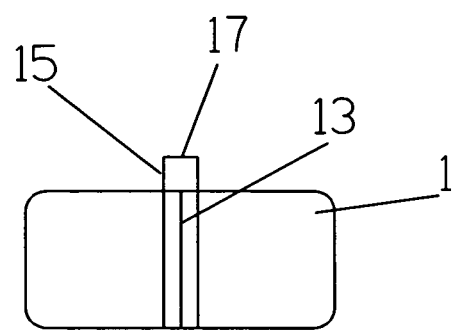
FIG. 21. is a top view of one embodiment of the aiming device.

FIG. 21 is a top view of one embodiment of the first platform (1) comprising a relatively stiff plastic or composite material and further comprising the marginal ridge angulation locator (13) and the angulation indicator (15) and the attachment stud on the angulation indicator (17) to which the angulation indication extension (18) and subsequently aiming platform (54) are attachable. After placing a bitewing x-ray sensor holder or film holder not comprising a marginal ridge angulation locator (13) in a human mouth and stabilizing it against the mandibular teeth, the first platform (1) of the present embodiment with the marginal ridge angulation locator (13) facing up is placed in the mouth with the marginal ridge angulation locator (13) seated into the occlusal groove (32) between two maxillary teeth, stabilized in that position while the patient closes the teeth together. The x-ray film or x-ray sensor holder stabilizing the film or sensor and the first platform (1) stabilizing the marginal ridge angulation locator (13) simultaneously and then the dental x-ray cone (27) may be aligned perpendicular to the plane of the aiming ring (22) and parallel to the aiming vector (19) for exposing the image. The first platform (1) of this embodiment comprising at least one of the marginal ridge angulation locator (13), the angulation indicator (15) the attachment stud on the angulation indicator (17), and a soft-sticky material similar to well chewed chewing gum (51) configured and formulated to help hold the marginal ridge angulation locator (13) in place over and aligned with the occlusal groove (32) until the teeth are closed in place to more firmly secure the marginal ridge angulation locator (13)

Figure 22:
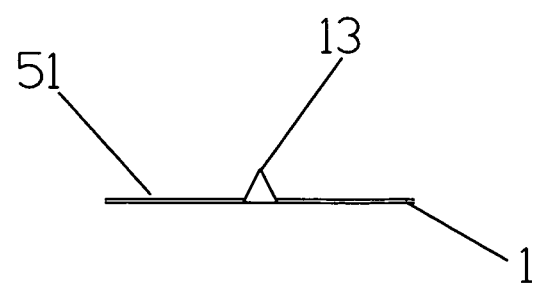
FIG. 22. is a lateral view of the same embodiment shown is FIG. 21.

FIG. 22 is a lateral side view of the same embodiment shown in FIG. 21 showing the first platform (1) with the soft stickey material (51) attached and the marginal ridge angulation locator (13).

Figure 23:
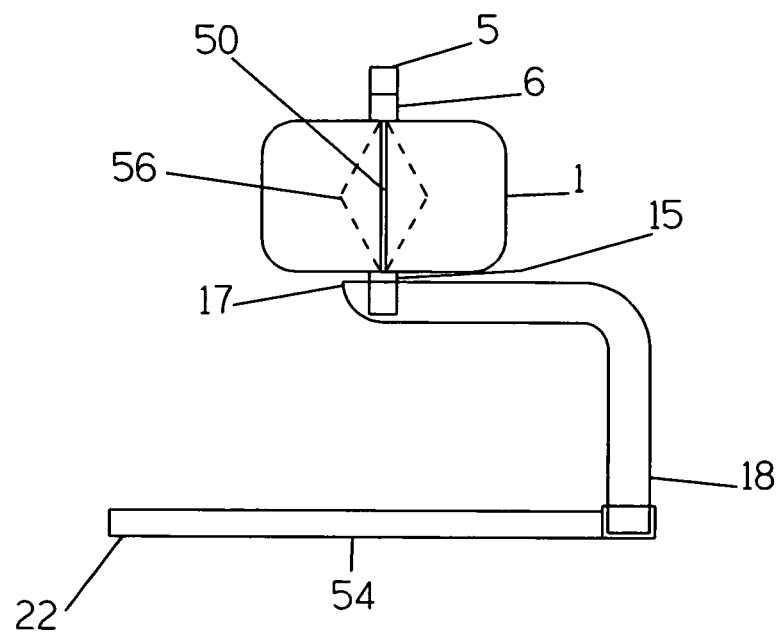
FIG. 23. is a top view of one embodiment of the aiming device.

FIG. 23 includes a top view of one embodiment of the first platform (1) comprising at least one of a clear or transparent, flexible plastic, composite and silicone rubber material. Further, the first platform (1) of this embodiment comprising a line (50) scribed and or colored so as to be easily visible from the operator's position outside the mouth enabling the occlusal groove to be visible through the first platform with the line visible superimposed over and aligned parallel to the occlusal groove (32) and the contact area (30) between the teeth. The first platform (1) further comprising the flexible pivot stud (6) positioned medial and parallel to the line (50) and the attachment end of the flexible pivot stud (5) which is attached to the medial end the flexible pivot stud (6) are located medial and parallel to the line (50). The attachment stud on the angulation indictor (17) to which the angulation indication extension (18) and subsequently the aiming platform (54) are capable of being attached and configured to facilitate the aiming of an x-ray beam (23) centered over and parallel to the aiming vector (19) defined by the line parallel to the contact area (30) on the first platform (1). The size of the first platform (1) could be reduced in any of the embodiments of the present invention to a small size first platform (56) outlined by the dotted line and possibly even much smaller for some embodiments.

Figure 24:
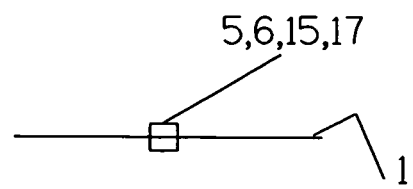
FIG. 24. is a lateral view of the same embodiment shown in FIG. 23.

FIG. 24 is a lateral side view of the first platform of the same embodiment as in FIG. 23 showing the angulation indicator (15) and the attachment stud on the angulation indicator (17).

Figure 25:
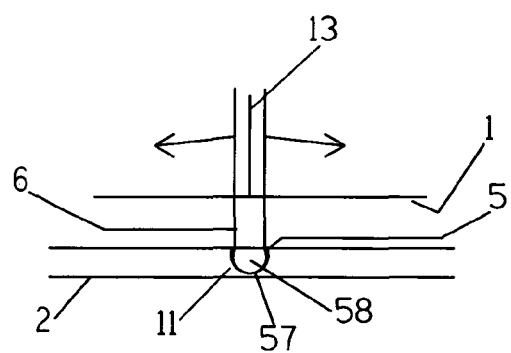
FIG. 25 is a top view of one embodiment of the aiming device.

FIG. 25 shows a top view of the attachment end (5) on the flexible pivot stud (6) of the first platform (1) removably, rotatably and flexibly connected to the second platform (2) in one embodiment of the present invention. This embodiment comprising a substantially cylindrically shaped attachment end (5) of the flexible pivot stud (6) is configured to fit into a corresponding shaped central attachment location (11) or another of a plurality of attachment locations (12) on the second platform (2). The central attachment location (11) comprising a negative cylindrically shaped space (57) with a long axis (58). The long axis (58) of the cylindrically shaped space (57) configured to be substantially perpendicular to the plane of the first platform (1) when the first platform (1) is attached to the second platform (2) and allow a rotation range of movement of the cylindrically shaped attachment end (5) of approximately 10 to 15 degrees or more around the long axis (58) of the cylindrically shaped space (57). Additionally the shape of the attachment end (5) comprising a shape that allows attachment end (5) and the flexible pivot stud (6) simultaneously to be only slightly movable in a vertical plane by as much as 2 to 5 degrees. This configuration of elements in this embodiment minimizes undesirable rotational movement of the flexible pivot stud (6) around the long axis of the marginal ridge angulation locator (13) and allows desirable range of motion in the horizontal plane (parallel to the plane of occlusion) and allows less desirable movement in a vertical plane (perpendicular to the plane of occlusion).

Figure 26:
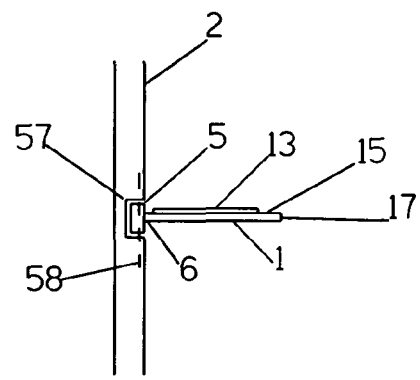
FIG. 26. is a side view of the same embodiment shown in FIG. 25.

FIG. 26 shows an end view of the same embodiment shown in FIG. 25 with the second platform (2) and the cylindrically shaped space (57) containing the cylindrically shaped attachment end (5) of the flexible pivot stud (6) that is attached to the first platform. Also shown is the long axis (58) of the cylindrically shaped space, which would coincide with the long axis of the cylindrically shaped attachment end (5) of the flexible pivot stud (6).

Figure 27:
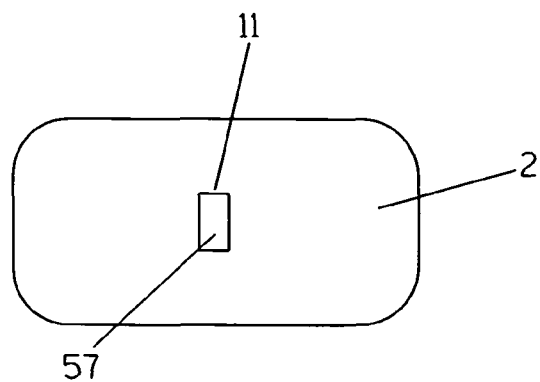
FIG. 27. is a lateral view of the same embodiment shown in FIG. 25 and FIG. 26.

FIG. 27 shows a lateral side view of the same embodiment shown in FIGS. 25 and 26 showing the second platform (2) and the central attachment location (11) and the cylindrically shaped space (57).

Figure 28:
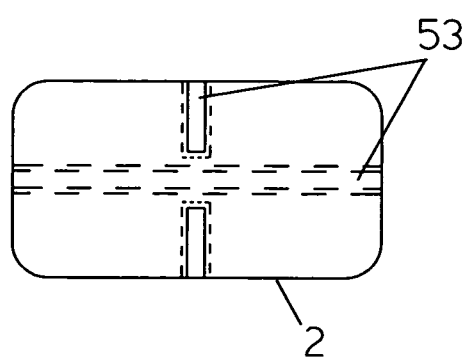
FIG. 28. is a lateral view of the second platform of one embodiment of the aiming device.

FIG. 28 a lateral side view of the second platform of one embodiment of the current invention. The second platform in this embodiment comprising as many as three or more non-intersecting dovetailed or other retentive shape slots (53) allowing a corresponding shaped attachment end (5) of the flexible pivot stud (6) to be slidably inserted into one end of the retentive shaped slot (53) and forcibly moved by sliding it in the retentive shaped slot (53). The retentive shaped slots (53) and corresponding attachment end (5) comprise cross sectional shapes configured to allow sliding movement of the attachment end (5) inside the retentive shaped slot (53) without allowing rotational movement of the attachment end (5) relative to the second platform (2) which further comprises at least one retentive device (24).

Figure 29:
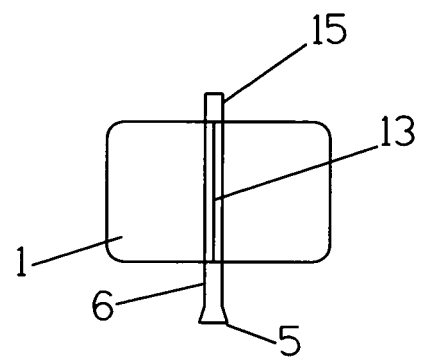
FIG. 29. is a top view of the first platform of the same embodiment shown in FIG. 28.

FIG. 29 is a top view of the first platform of the same embodiment as shown in FIG. 28. The first platform (1) comprising the attachment end (5) of the flexible pivot stud (6) further comprising a dovetail cross section configured to allow the attachment end of the flexible pivot stud (5) to slide into one of the dovetail cross sectioned grooves or retentive shaped slots (53) in the second platform (2) FIG. 28 to facilitate the exposing of horizontal bitewing x-rays, vertical bitewing x-rays and peri-apical x-rays in both the vertical and the horizontal orientations while allowing a continuous or non indexed range of adjustment of the relationship, mesially or distally, between the first platform (1) relative to the second platform (2).

Figure 30:
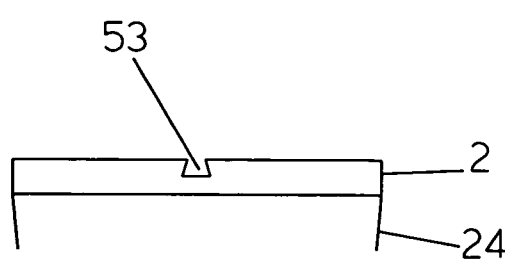
FIG. 30. is a top view of the second platform of the embodiment shown in FIG. 28.

FIG. 30 is a top view of the second platform of the same embodiment shown in FIGS. 28 and 29 comprising a dovetail cross section retentive shaped slot (53) and at least one retention device (24) to hold a dental x-ray sensor #25 or dental x-ray film (26). Configured in this manner the first platform (1) shown in FIG. 29 comprises almost unlimited range of position relative to the second platform (2) shown in FIGS. 28 and 30 to facilitate the taking of vertical bite wing horizontal bite wing, vertical peri apical and horizontal peri apical radiographs.

Figure 31:
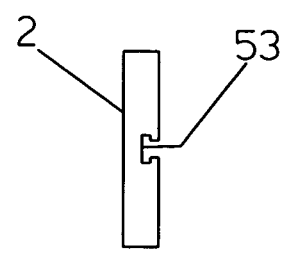
FIG. 31. is a side view of the second platform of the same embodiment shown in FIG. 28, FIG. 29, and FIG. 30.

FIG. 31 is an end view of the second platform (2) of the same embodiment shown in FIGS. 28, 29 and 30 with a different cross section retentive shaped slot (53) capable of mating with an appropriately configured attachment end (5) of the flexible pivot stud (6) of the first platform (1).

Figure 32:
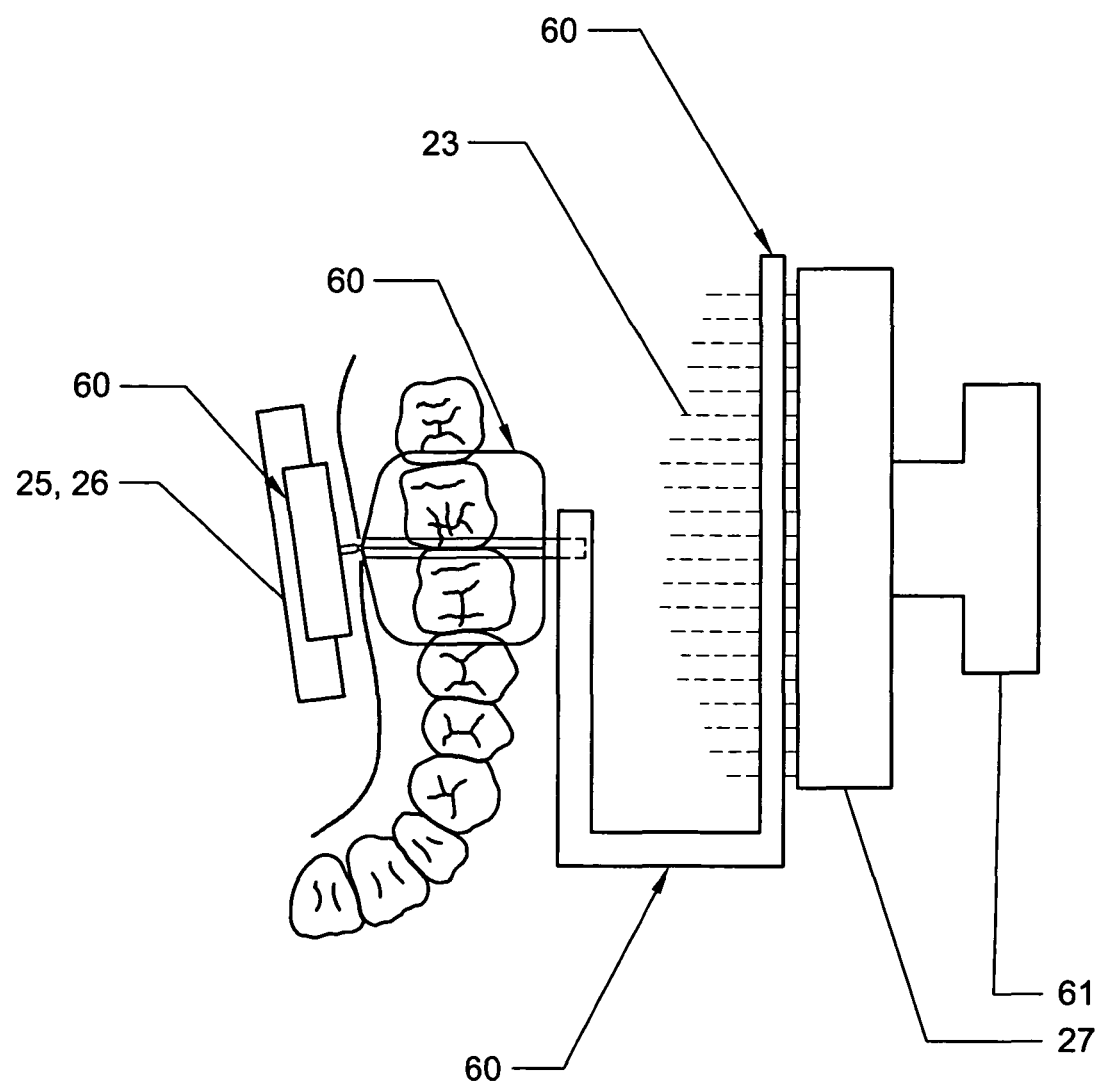
FIG. 32 is a schematic drawing for a system for taking dental x-rays.

FIG. 32 According to a preferred embodiment of a system for taking digital and or film based radiographic images includes a dental x-ray sensor (25) or dental x-ray film packet (26) retained or attached to an aiming fixture (60) capable of holding said dental x-ray film packet (26) and or said dental x-ray sensor (25) stabilized inside a human mouth and capable of conveying aiming information. For example, the aiming information could include position and angulation of the teeth or bone to be imaged and angulation of the contact area between teeth. An x-ray machine (61) with an x-ray cone (27) could then be aimed at the portion of the aiming device visible from outside the mouth. Once the x-ray cone (27) has been aligned to the aiming fixture (60) and the x-ray machine triggered the x-ray beam (23) emits from the x-ray cone (27) passing through the teeth and bone registering an image on the dental x-ray film packet (26) and or the dental x-ray sensor (25). In the case of the dental x-ray sensor, the image is digitally transmitted to a computer cpu through an electronic connection or wires connecting the computer and the dental x-ray sensor (25). The computer and CPU process the electronic information with software that allows storage, printing, or viewing the image.

We claim:

1. A fixture for aligning dental x-rays to be substantially parallel to the area between two adjacent teeth where said two adjacent teeth contact each other for exposing at least one of a dental radiographic film and a dental radiographic sensor comprising:

A first platform configured to fit and be stabilized between the biting surfaces of maxillary and the biting surfaces of mandibular teeth, comprising a superior or top surface and an inferior bottom surface; and A second platform comprising a medial surface and a lateral surface with an attachment location at the center of the lateral surface;

The first platform further comprising a flexible pivot stud with an attachment end capable of flexibly attaching said first platform to the attachment location on the second platform; wherein The first platform when attached to the second platform is oriented substantially perpendicular to the second platform and able to move 10 to 15 degrees of rotation in either direction about an axis of rotation perpendicular to the first platform and the flexible pivot stud and parallel to the plane of the second platform, The first platform further comprising a marginal ridge angulation locator capable of fitting into and being aligned with the substantially triangular cross-section shaped space that runs from the buccal aspect to the lingual aspect of human teeth on the biting surface of the human teeth between adjacent marginal ridges of adjacent teeth and thus locating an aiming vector, The marginal ridge angulation locator further comprising an angulation indicator that indicates a first vector that is parallel to the aiming vector and may be centered over the aiming vector, wherein The second platform is capable of securely holding a dental x-ray sensor or dental x-ray film packet against its medial surface, wherein when the second platform is attached to the first platform an x-ray beam aligned parallel to and centered over the marginal ridge angulation location indicator when the marginal ridge angulation locator bar is stabilized in the space on the occlusal surfaces of the teeth between the marginal ridges of two adjacent teeth, can expose said dental x-ray film or dental x-ray sensor with x-rays that have passed through the space between the adjacent teeth and expose an image of those two substantially distinct and non-overlapped teeth.

2. The fixture of claim 1, wherein the second platform has a plurality of attachment locations, each configured and positioned to facilitate the attachment of the first platform in a location and orientation that facilitates the attachment of the first platform in a location and orientation facilitating the taking of at least one of a horizontal bite wing x-ray, a vertical bite wing x-ray, and a horizontal peri-apical x-ray and a vertical peri-apical x-ray, and wherein the plurality of attachment locations comprises 5 or more attachment locations.

3. The fixture of claim 2 wherein the second platform has the plurality of attachment locations on its lateral surface, each configured as a hole.

4. The fixture of claim 3 wherein the holes have a square, round, octagonal or other cross-section.

5. The fixture of claim 3 further comprising an insert end on said pivot stud that is configured so that the insert end may be removably inserted into one of the holes in the lateral surface of the second platform, removed from the hole, and reinserted into the same or different hole in the lateral surface of the second platform at any chosen angle permitted by the shapes of the hole and the insert end.

6. The fixture of claim 4 wherein the relative shapes of an insert end of the pivot stud and a hole in the second platform into which the insert end is inserted, allow the first platform an angular range of movement relative to the lateral surface of the second platform of at least 5 degrees up to 15 degrees.

7. The fixture of claim 3 wherein the plurality of attachment locations on the second platform comprise another shape occupying positive space, for example a stud.

8. The fixture of claim 4 wherein the pivot stud comprises an insert end and the insert end further comprises a hole.

9. The fixture of claim 1 wherein the marginal ridge angulation locator comprises a triangular cross section, a nearly triangular cross section, a round cross section, a semi-round cross section, or any other shape cross section configured to fit into the somewhat triangular space between the marginal ridges on the biting surface of two adjacent teeth and capable of locating an aiming vector that is parallel to the area of contract between the two adjacent teeth.

10. The fixture of claim 1 further comprising an angulation indicator attached to the first platform and capable of defining a first vector parallel to the aiming vector, said angulation indicator comprising an attachment end to which an angulation indication extension may be permanently or removably attached.

11. The fixture of claim 10 wherein the angulation indication extension has either a straight or bent configuration, and indicates a second vector that is parallel to the first vector and the aiming vector that may be displaced in an anterior position relative to the first vector and the aiming vector allowing the second vector to be more visible from outside the mouth.

12. The fixture of claim 10 wherein the angulation indication extension comprises a ring or disc shaped device capable of being permanently or removably attached, wherein when the device is attached to the angulation indication extension the device may be centered over the aiming vector and the plane of the device may be located perpendicular to the aiming vector.

13. The fixture of claim 12 wherein the ring or disc shaped device is capable of being attached to a rod co-located with the second vector and configured in a manner allowing said device to slide along said rod, thus positioning said ring or disc shaped device to remain perpendicular and centered over the aiming vector, said device capable of being fixed at various distances from the platform.

14. A system for taking dental radiographs comprising:
An x-ray generating device or x-ray machine;
A dental x-ray sensor and/or dental x-ray film;
At least one of an x-ray view box and a viewing device comprising a computer and a software program to convert the information registered by the dental x-ray sensor so that it can be viewed on a video screen or printed and viewed;
At least one of a dental x-ray film packet holder and a dental x-ray sensor holder comprising at least one attachment location at the center of the lateral surface of the dental x-ray film packet holder or dental x-ray sensor holder; and
The fixture for aligning dental x-rays as claimed in claim 1.

15. A method for exposing dental x-ray film and/or a dental x-ray sensor, using the fixture of claim 10, that enables creating a clear image of the area of contact between two adjacent teeth showing the area where the two adjacent teeth contact each other where the adjacent teeth are seen as substantially individual teeth, distinct from one another and without the images of those two adjacent teeth being overlapped, the method comprising the steps of:
Attaching a dental x-ray sensor or dental x-ray film packet to the second platform and firmly securing it;
Attaching the pivot stud to the central attachment location on the lateral surface of the first platform in a configuration such that the marginal ridge angulation locator is facing up if the contact area to be viewed is the maxillary arch and the long direction of the dental film packet or dental x-ray sensor, when affixed to the second platform, is parallel to the occlusal plane of the teeth;
Positioning the marginal ridge angulation locator into the substantially v-shaped groove defined by the contact between two adjacent marginal ridges of the two adjacent teeth to be imaged so that the lateral end of the marginal ridge angulation locator is at least barely visible on the buccal side of the teeth to be imaged, and the second platform is located to the lingual of the mandibular or maxillary teeth, then having the patient bite together seating the marginal ridge angulation locator tightly into the substantially v-shaped groove between the adjacent marginal ridges of the two adjacent teeth stabilizing the fixture in that position;
Attaching the angulation indication extension to the angulation indicator so that the angulation indication extension is visible from outside the mouth;
Aiming the x-ray cone toward the angulation indicator centered over the aiming axis and aimed parallel to the aiming axis; and
Triggering the x-ray machine causing the x-rays to be emitted on a vector substantially parallel to the aiming vector and parallel to the contact area between adjacent teeth, causing the creation of an image showing the areas where the two adjacent teeth contact each other as substantially individual teeth in which the images of the teeth are distinct from each other and not superimposed.

16. The fixture of claim 1 the first platform is either flexibility or non-flexibly attached to the second platform, the marginal ridge angulation locator has a substantially triangular cross section and is configured to rotatably attach to the superior surface of the first platform, the angulation indicator comprising an attachment end to which an angulation indication extension may be attached, the axis of rotation of the marginal ridge angulation locator being oriented substantially parallel to the long axis of the teeth that hold the first platform when it is securely held between the maxillary and mandibular teeth, the marginal ridge angulation locator locating the aiming vector when it is rotated to a position where it lies in the substantially v-shaped groove between the adjacent marginal ridges of two adjacent teeth, and the angulation indication extension being attached to the marginal ride angulation locator to facilitate locating the aiming vector from outside the mouth.

17. The fixture of claim 10 wherein the first platform is permanently and non-flexibly attached to the second platform, the marginal ridge angulation locator device is flexibly attached to the lateral surface of the second platform so that it lies touching or nearly touching the superior surface with one of its flat sides, the marginal ridge angulation locator is configured to allow itself to be flexed so that it can lie in the substantially triangular cross sectional space between the adjacent marginal ridges of two adjacent teeth and locate the aiming vector, and the angulation indicator and angulation indicator extension may be attached to the marginal ridge angulation locator to facilitate locating and aiming x-rays centered over and parallel to the aiming vector from outside the mouth.

18. The fixture of claim 1 comprising a removable attachment between the first platform and the second platform further comprising an insert end on the pivot stud that is configured to removably insert into one of the holes in the lateral surface of the first platform, wherein the attachment comprises an insert end that is roughly square in cross-section, the greatest width w of the insert end is located at a distance that is equal to ½ the width w from the medial end of the insert end and the medial end conforms to an arc of radius ½ w with its center of rotation ½ w from each side and from the end of the insert end, the insert end tapers toward its center by 8 to 12 degrees, further comprising retention hinge depressions at the centers of rotation of the arcs on the top and bottom of the insert ends, wherein the second platform has a negative space configured to receive the medial end of the insert end, further comprising retention hinge studs configured to be located in the retention hinge depressions, wherein the anterior and posterior walls of the negative space have a length that will allow a 10-15 degree range of motion of the first platform and its attached marginal ridge angulation locator in the plane of occlusion.

19. The fixture of claim 1 wherein the parts of the fixture are molded of different materials including a material that be sterilized and a material not suitable for sterilization, which may include a metallic substance, a relatively stiff plastic, a relatively flexible plastic, a rubberlike material, and a composite material.

20. The fixture of claim 1 comprising a marginal ridge angulation locator that has a very thin triangular cross section wherein the height is greater that the base, wherein the apex of the marginal ridge locator comprises a hard material such as a metal or composite configured to allow the apex of the marginal ridge angulation locator to fit into and locate the aiming vector using the small space on the occlusal surface between two severely worn teeth.

21. The fixture of claim 1 further comprising a soft and compressible material on the surfaces of the first platform that also surrounds and abuts the marginal ridge angulation locator, allowing an operator to feel the relatively harder apex of the marginal ridge angulation locator seat into the very hard relatively v-shaped space between the marginal ridges of two adjacent teeth.

22. The fixture of claim 1 further comprising a marginal ridge angulation locator that has either a continuous bar shaped configuration or an interrupted bar shaped configuration thus reducing the overall radio opacity of the marginal ridge angulation locator bar as viewed from the lateral end.

23. The fixture of claim 22 comprising the marginal ridge angulation locator bar with the angulation indication extension not attached in any way to the second platform or the first platform, but configured to be placed independently in the mouth and locate and indicate the aiming angle to be seen from outside the mouth.

* * * * *